United States Patent
Morgan

(10) Patent No.: US 6,973,351 B2
(45) Date of Patent: Dec. 6, 2005

(54) LEADS USING COMPOSITE MATERIALS FOR CONDUCTORS AND STYLET INSERTION FOR IMPROVED HANDLING CHARACTERISTICS IN LEAD IMPLANTATION PERFORMANCE

(75) Inventor: Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 574 days.

(21) Appl. No.: 10/101,782

(22) Filed: Mar. 19, 2002

(65) Prior Publication Data

US 2003/0181966 A1    Sep. 25, 2003

(51) Int. Cl.⁷ .............................................. A61N 1/05
(52) U.S. Cl. ..................................... 607/122; 607/119
(58) Field of Search .................... 607/37–38, 115–116, 607/119, 122–123, 125; 600/372–374, 377, 600/381; 439/909

(56) References Cited

U.S. PATENT DOCUMENTS

| | | | |
|---|---|---|---|
| 4,498,482 A | 2/1985 | Williams | 128/786 |
| 4,643,202 A * | 2/1987 | Roche | 607/116 |
| 5,522,872 A * | 6/1996 | Hoff | 607/119 |
| 5,545,204 A | 8/1996 | Cammilli et al. | 607/123 |
| 5,851,226 A | 12/1998 | Skubitz et al. | 607/126 |
| 5,902,331 A | 5/1999 | Bonner et al. | 607/122 |
| 5,925,073 A | 7/1999 | Chastain et al. | 607/122 |
| 5,954,759 A * | 9/1999 | Swoyer et al. | 607/122 |
| 6,185,464 B1 | 2/2001 | Bonner et al. | 607/119 |
| 6,192,280 B1 | 2/2001 | Sommer et al. | 607/122 |
| 6,263,249 B1 | 7/2001 | Stewart et al. | 607/116 |
| 6,408,213 B1 | 6/2002 | Bartig et al. | 607/122 |
| 6,662,055 B1 | 12/2003 | Prutchi | 607/122 |
| 2001/0037135 A1 * | 11/2001 | Pianca et al. | 607/122 |
| 2003/0181966 A1 | 9/2003 | Morgan | 607/122 |

* cited by examiner

Primary Examiner—Robert E. Pezzuto
Assistant Examiner—Kristen Mullen

(57) ABSTRACT

An implantable lead for electrical stimulation of the body includes an elongated multi-lumen proximal tube composed of a first material having a first lumen for freely receiving a guidewire therethrough, a cable conductor extending between proximal and distal ends and received in a second lumen of the proximal tube, an elongated distal tube composed of a second material extending between proximal and distal ends having at least one lumen therein, a distal tip electrode attached to the distal end of the distal tube, a coil conductor received in the lumen of the distal tube extending between the proximal end thereof and the distal end thereof and being joined at the distal end to the distal tip electrode, and a joint assembly for electrically and mechanically connecting the distal end of the cable conductor to the proximal end of the coil conductor.

19 Claims, 5 Drawing Sheets

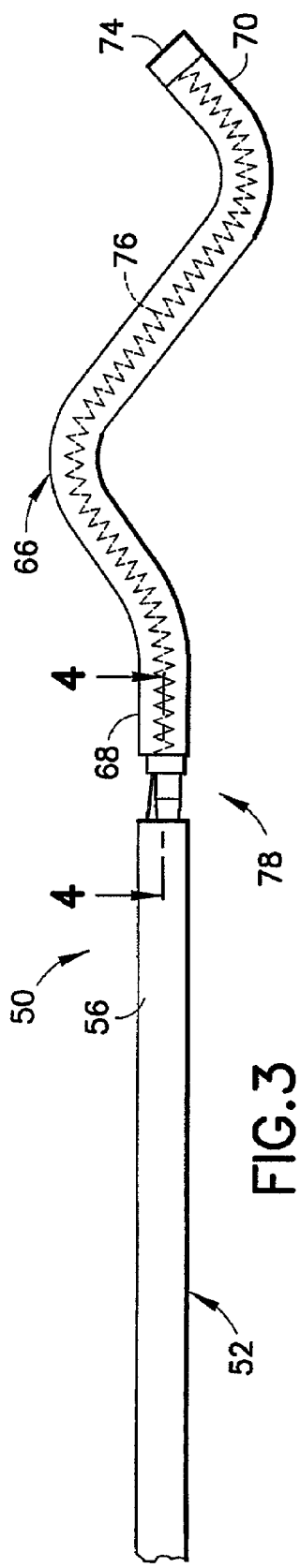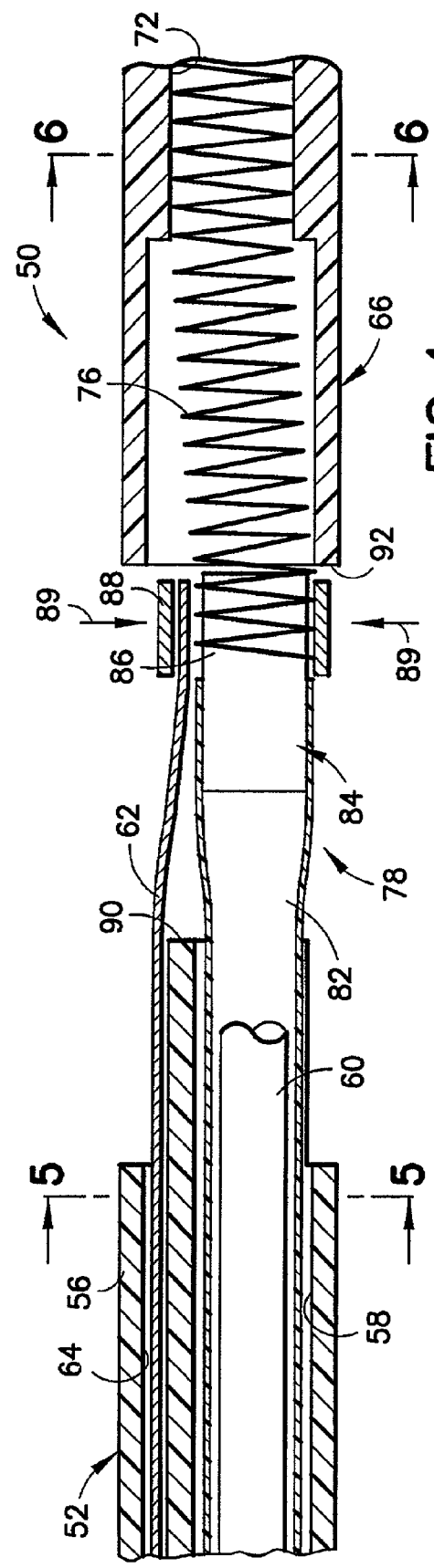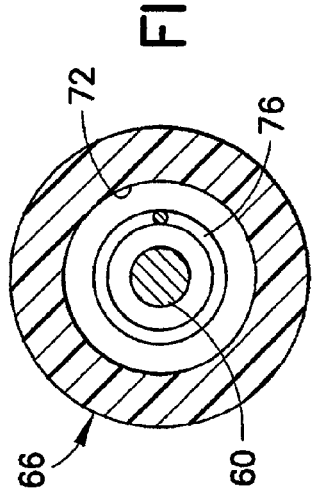

LEADS USING COMPOSITE MATERIALS FOR CONDUCTORS AND STYLET INSERTION FOR IMPROVED HANDLING CHARACTERISTICS IN LEAD IMPLANTATION PERFORMANCE

FIELD OF THE INVENTION

The present invention relates generally to implantable medical devices for providing stimulating pulses to selected body tissue, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled conductor surrounded by an insulating tube or sheath typically couples the connector pin at the proximal end and the electrode at the distal end.

The implantable cardiac stimulation leads with which the present invention is concerned may take the form of pacemakers capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator, commonly known as a "pacemaker" or "pacer", uses one or two flexible leads having one end connected to the pacer and the other end connected to electrodes placed in close proximity to the heart. These leads are used to stimulate or pace the heart. Also, these leads are used to sense the heart activity by picking up electrical signals from the heart.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer case or housing. The case, in turn, makes contact with the body tissue and/or fluids.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated about 10 to 20 mm from the tip electrode. The tip electrode is typically placed in contact with heart tissue, while the ring electrode is in electrical contact with the blood. Because both body tissue and fluids are conductive, the ring electrode of a bipolar lead, in contact with the body fluids, serves as an electrical return for both pacing and sensing.

As indicated, pacing or sensing using the pacer case or enclosure as part of the electrical return path is known as unipolar pacing or sensing. Pacing or sensing using the lead ring electrode and associated lead conductor as the electrical return path is known as bipolar pacing or sensing. There are numerous factors to consider when deciding whether unipolar or bipolar pacing and/or sensing should be used. Bipolar pacing has, in general, the advantage of requiring less energy than unipolar pacing. Further, bipolar sensing is less prone to crosstalk and myopotential sensing than is unipolar sensing. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is preferred if pectoral or diaphragmatic stimulation occurs.

Unipolar pacing and sensing offers the advantage, in general, of simpler circuitry within the pacemaker and a smaller diameter lead. Some physicians prefer unipolar over bipolar pacing and/or sensing as a function of other implantation and heart conditions. Depending on the lead orientation, unipolar sensing may be preferable to bipolar sensing.

In any event, cardiac pacing leads intended to be placed in the chambers of the heart or the coronary venous system are subjected to a series of tortuous bends. The leads must have the flexibility to follow these bends but have a enough structural support to allow the leads to be pushed and twisted in order to navigate within these veins. Creating a lead that has a proximal end of polyurethane and a distal end made out of silicone helped solve this problem.

Changing the coil winding to a PTFE (polytetrafluoroethylene) liner for stylet and/or guidewire insertion solved the stylet/guidewire jamming problem as taught in U.S. patent application Ser. No. 09/797,531, filed Feb. 28, 2001, entitled "Lead with Polymeric Tubular Liner for Guidewire and Stylet Insertion", the disclosure of which is incorporated herein in its entirety. This, however, changed the characteristics of the lead. Having a PTFE liner for guidewire passage from end to end on a lead made the lead too stiff at the distal end. This caused the lead to lose the flexibility needed the track over the guidewire.

For the purpose of clarity, the term "guidewire" will be used to denote the components technically known as stylets and guidewires throughout the remainder of this disclosure.

Typical of the known prior art is U.S. Pat. No. 5,851,226 to Skubitz et al., which discloses an implantable lead system, which includes a lead body and a guide body. The lead body is limp for optimal post implantation characteristics and the guide body is torqueable for optimal implantation. U.S. Pat. Nos. 6,185,464 and 5,902,331 to Bonner et al. disclose similar lead systems, which provide a guide body, which is external to the lead during the implantation procedure. U.S.

Pat. No. 6,263,249 to Stewart et al. discloses an implantable lead system, which is provided with a surface texture to increase slip during implantation.

It was in light of the foregoing that the present invention was conceived and has now been reduced to practice.

SUMMARY OF THE INVENTION

An implantable lead for electrical stimulation of the body includes an elongated multi-lumen proximal tube composed of a first material having a first lumen for freely receiving a guidewire therethrough, a cable conductor extending between proximal and distal ends and received in a second lumen of the proximal tube, an elongated distal tube composed of a second material extending between proximal and distal ends having at least one lumen therein, a distal tip electrode attached to the distal end of the distal tube, a coil conductor received in the lumen of the distal tube extending between the proximal end thereof and the distal end thereof and being joined at the distal end to the distal tip electrode, and a joint assembly for electrically and mechanically connecting the distal end of the cable conductor to the proximal end of the coil conductor.

This invention provides a lead for left side pacing and/or defibrillation which utilizes a polyurethane and silicone outer insulation materials. A PTFE tube and a coil winding are joined together in the inner lumens of the outer insulating materials for stylet or guidewire placement.

The PTFE liner is within the polyurethane insulation and the coil winding is placed within the silicone insulation. This gives the lead the right amount of stiffness for torqueability and pushability while having a flexible distal end for steerability and control.

This invention is then:

1. a lead for the left side placement of the heart that utilizes a dual system of PTFE tubing and coil winding for guidewire and/or stylet insertion;
2. a lead for the left side placement of the heart that utilizes a dual system of cable and coil conductors for the transport of electrical energy to the tip electrode;
3. a lead for the left side placement of the heart that has a proximal lead body that is stiff enough to allow the transfer of torque through the lead to give the lead steerability;
4. a lead for the left side placement of the heart that has a degree of pushability to help advance the tip electrode to the target site;
5. a lead for the left side placement of the heart that has a flexible distal section that allows the lead to track the veins of the heart;
6. a lead for the left side placement of the heart that has a flexible distal section that allows the lead to glide easy over the guidewire or stylet;
7. a lead for the left side placement of the heart that has a method of joining two dissimilar materials to allow a guidewire or stylet to pass through (PTFE tubing and coil winding); and
8. a lead for the left side placement of the heart that has a method of joining two dissimilar conductors (cables to coil winding).

A primary feature, then, of the present invention is the provision of a lead assembly connecting an implantable medical device with the tissue to be stimulated exhibiting improved handling characteristics during implantation.

Another feature of the present invention is the provision of such an improved lead assembly employing a system of PTFE tubing and coil winding for guidewire and/or stylet insertion.

Yet another feature of the present invention is the provision of such an improved lead assembly employing a dual system of cable and coil conductors for the transport of electrical energy to the tip electrode.

Still another feature of the present invention is the provision of such an improved lead assembly that allows the lead to track the veins of the heart.

Still a further feature of an improved lead assembly is the provision of such an improved lead assembly that allows the lead to glide easy over the guidewire or stylet.

Yet a further feature of the present invention is the provision of such an improved lead assembly constructed by a method of joining two dissimilar materials to allow a guidewire or stylet to pass through PTFE tubing and a coil winding.

Yet another feature of the present invention is the provision of such an improved lead assembly which utilizes a method of joining two dissimilar conductors, such as a cable to a coil winding.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is a detail elevation view of a portion of the lead system illustrated in FIG. 2;

FIG. 4 is a cross-section view taken generally along line 4—4 in FIG. 3;

FIG. 6 is a cross-section view taken generally along line 6—6 in FIG. 4;

DETAILED DESCRIPTION OF THE PREFERRED EMBODIMENT

Figure 1:
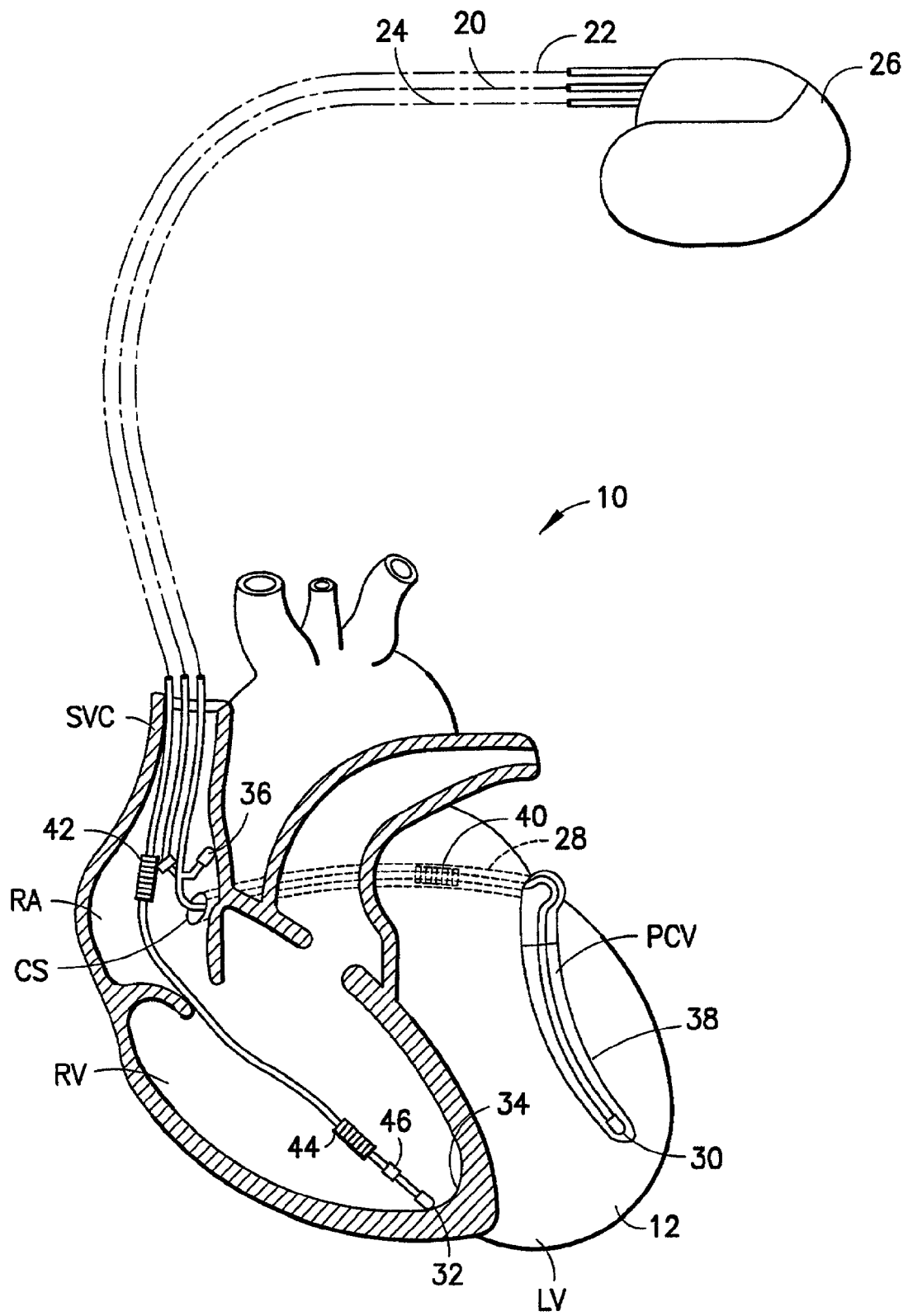
FIG. 1 is a diagrammatic perspective view illustrating an implanted lead system for providing electrical stimulation of a heart employing an implanted lead embodying the present invention.
Figure 2:
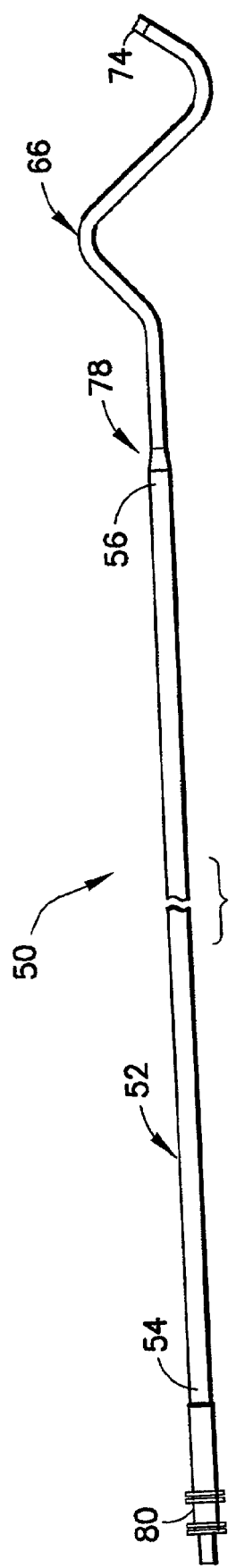
FIG. 2 is an elevation view of a portion of the lead system illustrated in FIG. 1.

Refer now to the drawings and, initially, to FIG. 1 in which is shown a diagrammatic perspective view of an implanted system 10 for providing electrical stimulation of a heart 12 incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

In FIG. 1, there are also illustrated implantable leads 20, 22, 24 generally embodying the invention for stimulation of the body, the heart 12 in this instance, by means of a pacemaker 26 or other suitable pulse generating device. This is a cross section view of a human heart showing the right atrium RA and the right ventricle RV along with the coronary sinus CS and a vein 28 of the left side of the heart. This vein of the left side could be any of the veins found on the left side of the heart such as the Great Cardiac Vein, Posterior Vein, or the Lateral Vein of the left ventricle LV. The leads are shown in a typical placement, lead 20 being an RA lead, lead 22 being an RV lead, and lead 24 being an LV lead inserted via the superior vena cava SVC into the coronary sinus ostium CSO located in the right atrium RA. The lead 24 is then advanced through the coronary sinus ostium passing through the coronary sinus and placed into a tributary of the coronary venous system, preferably the left posterior cardiac vein PCV with an associated tip electrode 30 being placed deep in the distal portion of the left side of the heart. The phrase "coronary venous system" refers to the coronary sinus vein, great cardiac vein, left marginal vein, left posterior vein, middle cardiac vein, and/or small cardiac veins or any other cardiac vein accessible by the coronary sinus. From this location, the lead 24 can be used to stimulate the left ventricle LV. Clearly, the lead 24 must follow a tortuous path in order for the tip electrode 30 to reach its intended destination. The lead 22 extends to a tip electrode 32 placed in the apex 34 of the right ventricle RV and illustrates the typical position of a lead in the right ventricle. The lead 20 extends to a tip electrode 36 shown in the appendage of the right atrium RA and illustrates the typical position of the lead in the appendage of the right atrium. In this scenario, component 38 is typical of a sensing electrode of the LV lead 24, component 40 is typical of a shock electrode of the LV lead 24, component 42 is typical of a proximal shock coil of the RV lead 22, component 44 is typical of a distal shock coil of the RV lead 22, and component 46 is typical of a ring electrode of the RV lead 22.

The thrust of the present invention is to provide an implantable lead which will readily negotiate the tortuous paths of the heart or other organ of the body which are necessary in order for an electrode to reach its intended destination.

Turn now to FIGS. 2–6 for the description of a novel implantable lead 50 for electrical stimulation of the body, which specifically embodies the present invention. The lead 50 includes an elongated multi-lumen proximal tube 52 composed of a first material extending between proximal and distal ends 54, 56 and having a first lumen 58 for freely receiving a guidewire 60 throughout its length. A cable conductor 62 similarly extending between proximal and distal ends is received in a second lumen 64 of the proximal tube 52.

In a similar manner, an elongated distal tube 66 composed of a second material extends between proximal and distal ends 68, 70, respectively, and has at least one lumen 72, also for freely receiving the guidewire 60 throughout its length. A distal tip electrode 74 is attached to the distal end 70 of the distal tube and a coil conductor 76 is received in the lumen 72 extending between the proximal and distal ends 68, 70, being suitably joined at the distal end to the distal tip electrode 74. A joint assembly 78 serves to electrically and mechanically connect the distal end of the proximal tube 52 and its cable conductor 62 to the proximal end of the distal tube 66 and its coil conductor 76.

Turning back to FIG. 2, it is seen that the implantable lead 50 includes an electrically conductive proximal pin 80, preferably of an IS-1 configuration, distant from the tip electrode 74 and the proximal end of the cable conductor is suitably connected to the proximal pin.

An important component of the present invention is an elongated polymeric tubular liner 82 composed of a material having a coefficient of friction in the range of about 0.02 to about 0.20 extending between proximal and distal ends and received in the first lumen 58 of the proximal tube 52 for freely receiving the guidewire 60. A typical and preferred material is polytetrafluoroethylene (PTFE), sometimes referred to by the trademark Teflon®. A primary function of the polymeric tubular liner 82 is to freely receive the guidewire 60 in the lumen 58 of the proximal tube 52 before the guidewire is subsequently received in the lumen 72 of the distal tube 66. In the normal scheme of things, the guidewire is first implanted along the route subsequently intended for the lead 50, then the lead is introduced onto the guidewire and advanced, or tracked, to its final position. In this instance, the low coefficient of friction of the polymeric tubular liner 82 greatly facilitates the insertion process as compared with the use of previously known lead constructions. Additionally, the polymeric liner made of PTFE, for example, elongates minimally under an axial load, and in tubular form has a uniform inner and outer diameter. The lead 50, so modified, does not jam when using a guidewire and the lead tracks in a satisfactory manner over the guidewire through the tortuous bends of the veins of the left heart, for example.

Viewing especially FIGS. 3 and 4, the joint assembly 78 includes a conductive transition tube 84 which has an outer peripheral surface 86 and which is received in the distal end 56 of the proximal tube 52 and in the proximal end 68 of the distal tube 66. The distal end of the cable conductor 62 and the proximal end of the coil conductor 76 are positioned to overlie the outer peripheral surface 86 of the transition tube 84. Thereupon, a crimp tube 88 coaxial with the transition tube and coextensive with the region at which the distal end of the cable conductor and the proximal end of the coil conductor is positioned to overlie the outer peripheral surface of the transition tube, then suitably attached to the cable conductor, to the coil conductor, and to the transition tube. In one instance, for example, the crimp tube may be mechanically compressed into firm engagement, as indicated by arrows 89, with the cable conductor, the coil conductor, and the transition tube. In another instance, for example, the crimp tube may be attached by being welded to the cable conductor, the coil conductor, and the transition tube.

In any event, it will be recognized as particularly desirable that the joint assembly includes a reduced diameter distal end male portion 90 of the proximal tube 52 fittingly received in a generally similarly sized and shaped female portion 92 of the distal tube 66. Also, it will be appreciated that the elongated polymeric tubular liner 82 is fittingly attached at its distal end to the outer peripheral surface 86 of the transition tube 84.

It was earlier explained that because cardiac pacing leads intended to be placed in the chambers of the heart or the coronary venous system are subjected to a series of tortuous bends, they must have the flexibility to follow these bends but have a enough structural support to allow them to be pushed and twisted in order to navigate within these veins. The lead of the present invention meets these criteria. More specifically, the first material of the proximal tube 52 is characterized as having greater abrasion resistance and stiffness than the second material of the distal tube and the second material of the distal tube 66 is characterized as having greater flexibility and pliability than the first material of the proximal tube. In actual practice, this result may be achieved if the first material is polyurethane and if the second material is silicone.

Figure 9:
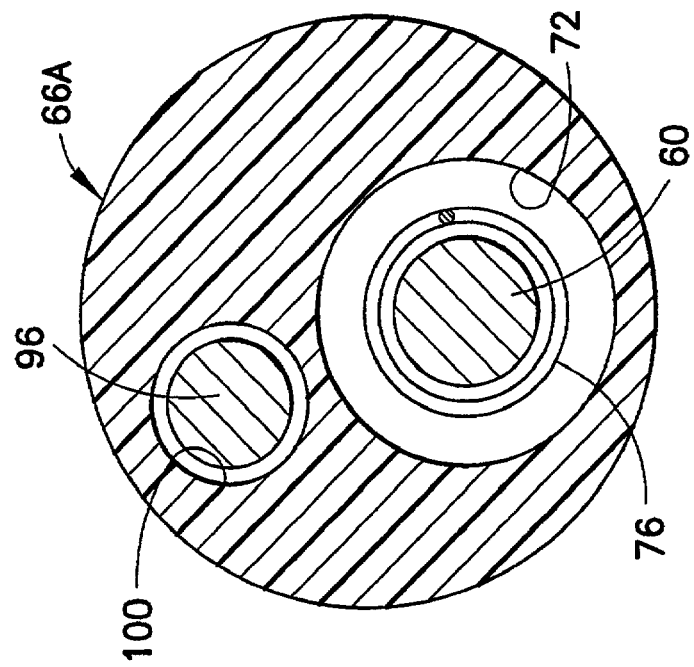
FIG. 9 is a cross-section view taken generally along line 9—9 in FIG. 8.
Figure 5:
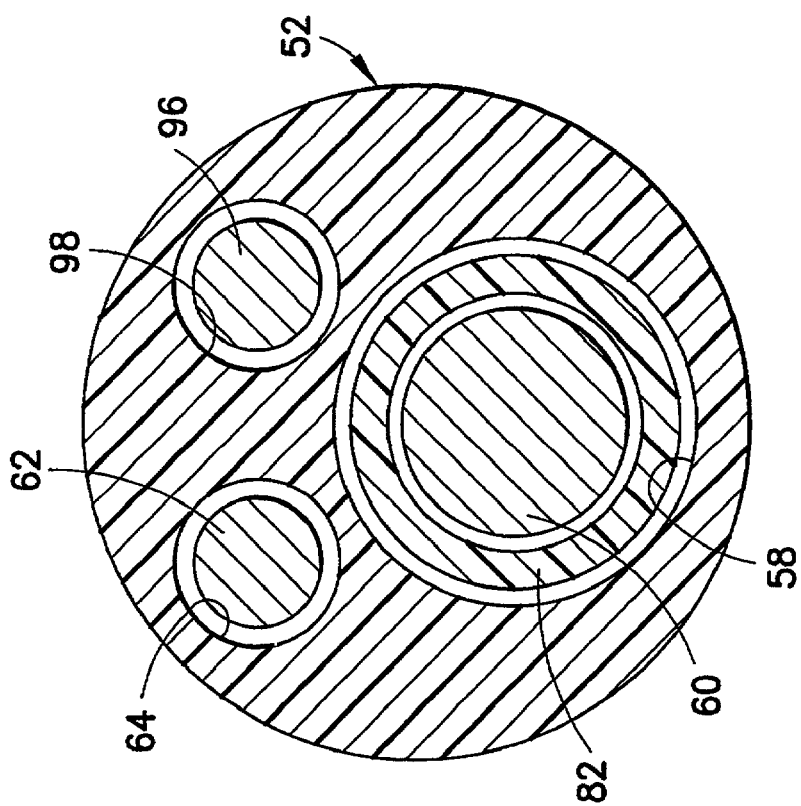
FIG. 5 is a cross-section view taken generally along line 5—5 in FIG. 4.
Figure 7:
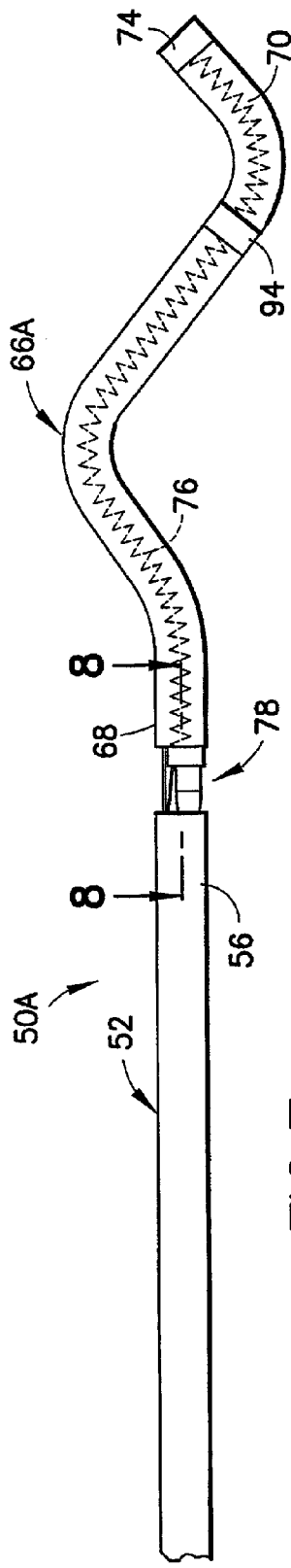
FIG. 7 is a detail elevation view of a portion of another embodiment of the lead system illustrated in FIG. 2.
Figure 8:
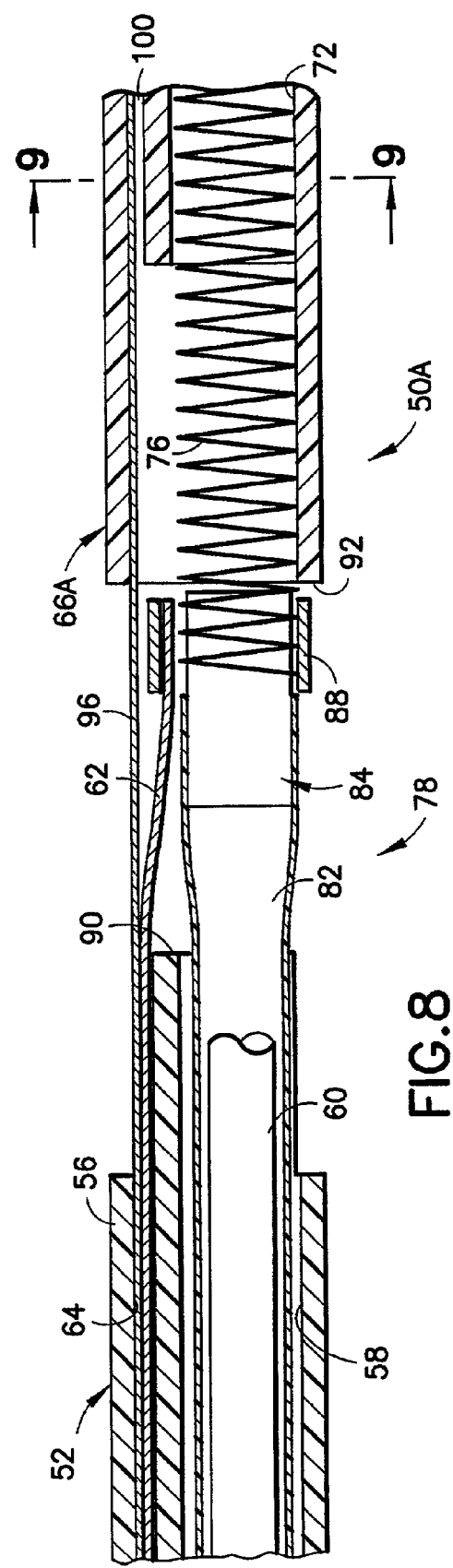
FIG. 8 is a cross section view taken generally along line 8—8 in FIG. 7.

Turn now to FIGS. 7, 8, and 9 for the description of another embodiment of the invention. The embodiment described above with the aid of FIGS. 2–6 presented a unipolar electrode configuration. The present embodiment is a bipolar electrode configuration. In this instance, a ring electrode 94 is attached to a modified distal tube 66A at a location proximally spaced from the distal tip electrode 74. A second cable conductor 96 extending between proximal and distal ends is received in a third lumen 98 of the proximal tube 52 and in a second lumen 100 of the distal tube 66 and is suitably connected to the ring electrode 94 at its distal end. The end result is a modified implantable lead 50A, which bears all the advantages of the lead 50 while being of the bipolar electrode configuration.

It should be understood that the foregoing description is only illustrative of the invention. Various alternatives and modifications can be devised by those skilled in the art without departing from the invention. Accordingly, the present invention is intended to embrace all such alternatives, modifications and variances, which fall within the scope of the appended claims.

What is claimed is:

1. A method of making a lead for electrical stimulation of the body comprising the steps of:
   (a) inserting into one lumen of an elongated multi-lumen proximal tube extending between proximal and distal ends an elongated polymeric tubular liner having a coefficient of friction in the range of 0.02 to 0.20 extending between the proximal and distal ends for the free reception therethrough of a guide wire;
   (b) inserting into another lumen of the elongated proximal tube a cable conductor extending between the proximal and distal ends;
   (c) inserting a coil conductor into a lumen of a distal tube extending between proximal and distal ends, a distal tip electrode being attached to the distal end of the distal tube;
   (d) joining the distal end of the coil conductor to the distal tip electrode;
   (e) joining a proximal end of the distal tube to a distal end of the proximal tube while electrically connecting the distal end of the cable conductor to the proximal end of the coil conductor.

2. A method as set forth in claim 1:
   wherein the proximal tube is composed of a material having greater abrasion resistance and stiffness than the material of the distal tube; and
   wherein the distal tube is composed of a material having greater flexibility and pliability than the material of the proximal tube.

3. A method as set forth in claim 1:
   wherein the proximal tube is composed of polyurethane; and
   wherein the distal tube is composed of silicone.

4. A method as set forth in claim 1 wherein steps (d) and (e) include the steps of:
   (f) inserting a conductive transition tube having an outer peripheral surface into the distal end of the proximal tube and into the proximal end of the distal tube;
   (g) positioning the distal end of the cable conductor and the proximal end of the coil conductor so as to overlie the outer peripheral surface of the transition tube;
   (h) positioning a crimp tube so as to be coaxial with the transition tube and coextensive with the region at which the distal end of the cable conductor and the proximal end of the coil conductor overlie the outer peripheral surface of the transition tube; and
   (i) attaching the crimp tube to the cable conductor, to the coil conductor, and to the transition tube.

5. A method as set forth in claim 4 wherein steps (d) and (e) include the step of:
   (j) forming a reduced diameter distal end male portion of the proximal tube so as to be fittingly received in a congruently sized and shaped female portion at the proximal end of the distal tube.

6. A method as set forth in claim 1 wherein the elongated polymeric tubular liner is composed of PTFE.

7. A method as set forth in claim 1 including the steps of:
   (f) attaching a ring electrode to the distal tube proximally spaced from the distal tip electrode;
   (g) inserting a second cable conductor extending between proximal and distal ends into a third lumen of the proximal tube and into a second lumen of the distal tube; and
   (h) connecting the second cable conductor at its distal end to the ring electrode.

8. An implantable lead for electrical stimulation of a body comprising:
   an elongated multi-lumen proximal tube comprising a first material and defining a first lumen for freely receiving a guidewire therethrough;
   a cable conductor received in a second lumen of the proximal tube;
   an elongated distal tube comprising a second material and defining at least one lumen therein;
   a distal tip electrode attached to the distal end of the distal tube;
   a coil conductor received in the lumen of the distal tube and being joined at the distal end to the distal tip electrode; and
   a joint assembly for electrically and mechanically connecting one end of the cable conductor to one end of the coil conductor;
   wherein the first material of the proximal tube is characterized as having greater abrasion resistance and stiffness than the second material of the distal tube; and
   wherein the second material of the distal tube is characterized as having greater flexibility and pliability than the first material of the proximal tube.

9. An implantable lead as set forth in claim 8 further comprising:
   an elongated polymeric tubular liner having a coefficient of friction in the range of about 0.02 to 0.20 extending between proximal and distal ends and received in the first lumen of the proximal tube for freely receiving the guidewire.

10. An implantable lead as set forth in claim 9 wherein the elongated polymeric tubular liner is composed of PTFE.

11. An implantable lead as set forth in claim 8 further comprising:

an electrically conductive proximal pin distant from the tip electrode; and wherein the proximal end of the cable conductor is connected to the proximal pin.

12. An implantable lead as set forth in claim 11 wherein the joint assembly comprises:

a reduced diameter distal end male portion of the proximal tube fittingly received in a generally similarly sized and shaped female portion at the proximal end of the distal tube.

13. An implantable lead as set forth in claim 8:

wherein the first material is polyurethane; and wherein the second material is silicone.

14. An implantable lead for electrical stimulation of a body comprising:

an elongated multi-lumen proximal tube comprising a first material and defining a first lumen for freely receiving a guidewire therethrough;

a cable conductor received in a second lumen of the proximal tube;

an elongated distal tube comprising a second material and defining at least one lumen therein;

a distal tip electrode attached to the distal end of the distal tube;

a coil conductor received in the lumen of the distal tube and being joined at the distal end to the distal tip electrode; and a joint assembly for electrically and mechanically connecting one end of the cable conductor to one end of the coil conductor;

wherein the joint assembly comprises:

a conductive transition tube having an outer peripheral surface received in the distal end of the proximal tube and in the proximal end of the distal tube;

the distal end of the cable conductor and the proximal end of the coil conductor overlying the outer peripheral surface of the transition tube;

a crimp tube coaxial with the transition tube and coextensive with the region at which the distal end of the cable conductor and the proximal end of the coil conductor overlie the outer peripheral surface of the transition tube, the crimp tube being attached to the cable conductor, to the coil conductor, and to the transition tube.

15. An implantable lead as set forth in claim 14 wherein the crimp tube is mechanically compressed into firm engagement with the cable conductor, the coil conductor, and the transition tube.

16. An implantable lead as set forth in claim 14 wherein the crimp tube is attached by welding to the cable conductor, the coil conductor, and the transition tube.

17. An implantable lead as set forth in claim 14 further comprising:

the elongated polymeric tubular liner extending between proximal and distal ends and received in the first lumen of the proximal tube for freely receiving the guidewire;

wherein the elongated polymeric tubular liner is fittingly attached at its distal end to the outer peripheral surface of the transition tube.

18. An implantable lead for electrical stimulation of a body comprising:

an elongated multi-lumen proximal tube comprising a first material and defining a first lumen for freely receiving a guidewire therethrough;

a cable conductor received in a second lumen of the proximal tube;

an elongated distal tube comprising a second material and defining at least one lumen therein;

a distal tip electrode attached to the distal end of the distal tube;

a coil conductor received in the lumen of the distal tube and being joined at the distal end to the distal tip electrode; and a joint assembly for electrically and mechanically connecting one end of the cable conductor to one end of the coil conductor;

wherein the joint assembly comprises a reduced diameter distal end male portion of the proximal tube fittingly received in a congruently sized and shaped female portion at the proximal end of the distal tube.

19. An implantable lead for electrical stimulation of a body comprising:

an elongated multi-lumen proximal tube comprising a first material and defining a first lumen for freely receiving a guidewire therethrough;

a cable conductor received in a second lumen of the proximal tube;

an elongated distal tube comprising a second material and defining at least one lumen therein;

a distal tip electrode attached to the distal end of the distal tube;

a coil conductor received in the lumen of the distal tube and being joined at the distal end to the distal tip electrode;

a joint assembly for electrically and mechanically connecting one end of the cable conductor to one end of the coil conductor;

a ring electrode attached to the distal tube proximally spaced from the distal tip electrode; and a second cable conductor extending between proximal and distal ends and received in a third lumen of the proximal tube and in a second lumen of the distal tube and connected to the ring electrode at its distal end.

* * * * *